United States Patent

Armand

[11] Patent Number: 5,136,097
[45] Date of Patent: Aug. 4, 1992

[54] PROCESS FOR THE PREPARATION OF SULFONYLMETHANES AND DERIVATIVES THEREOF

[75] Inventor: Michel Armand, S-Martin-d'Uriage, France

[73] Assignees: Centre National de la Recherche Scientifique, Paris, France; Hydro-Quebec, Montreal, Canada

[21] Appl. No.: 613,641

[22] PCT Filed: Apr. 5, 1990

[86] PCT No.: PCT/FR90/00241
§ 371 Date: Dec. 3, 1990
§ 102(e) Date: Dec. 3, 1990

[87] PCT Pub. No.: WO90/12000
PCT Pub. Date: Oct. 18, 1990

[30] Foreign Application Priority Data

Apr. 6, 1989 [FR] France ................... 89 04503

[51] Int. Cl.$^5$ ............... C07C 315/04; C07C 221/00; C07C 211/62
[52] U.S. Cl. .................. 568/28; 568/34; 568/35; 564/281; 564/282; 564/289; 564/291; 564/296
[58] Field of Search ............ 568/28, 29, 35, 34; 564/281, 282, 289, 291, 296

[56] References Cited

U.S. PATENT DOCUMENTS 3,776,960 12/1973 Koshar et al. .............. 568/35
3,932,526 1/1976 Koshar et al. .............. 568/35

FOREIGN PATENT DOCUMENTS 1309013 7/1973 United Kingdom .
1327205 8/1973 United Kingdom .
1465559 2/1977 United Kingdom .

*Primary Examiner*—Marianne Cintins
*Assistant Examiner*—Margaret J. Argo
*Attorney, Agent, or Firm*—Oblon, Spivak, McClelland, Maier & Neustadt

[57] ABSTRACT

The invention relates to a process for the synthesis of sulfonylmethanes and derivatives thereof of the formula $M[(RSO_2)_2CH]_m$ (I), in which M represents H, an alkali metal or alkaline earth metal or $NR'_4$, R' and R are monovalent organic radicals and m represents the valence of M.

The process comprises reacting an ionic carbide with a sulfonyl halide, hydrolyzing the product obtained, adding a compound $M_yY_m$, in which Y represents an anion capable of reacting with the cation of the ionic carbide to the reaction medium before or after hydrolysis to give a compound which can be separated from compound (I), and y represents the valence of Y.

14 Claims, No Drawings

PROCESS FOR THE PREPARATION OF SULFONYLMETHANES AND DERIVATIVES THEREOF

The present invention relates to a process for the synthesis of sulfonylmethanes and derivatives thereof, and more particularly of symmetrical perfluorosulfonylmethanes and derivatives thereof.

The perfluorosulfonylmethanes of the general formula $[(R_FSO_2)_2CH]_y$, in which M designates a metal or a quaternary or non-quaternary ammonium group, the $R_F$, which are identical in the case of symmetrical methanes or different in the case of unsymmetrical methanes, represent monovalent perfluorohydrocarbon radicals and especially perfluoroalkyl radicals, such as $CF_3$, $C_2F_5$, $C_4F_9$ or perfluoroaryl radicals, such as $C_6F_5$, and y is a number equal to the valence of M, are of interest, due to their properties connected with the corresponding anion. Indeed, delocalization of the charge of the anion over several electronegative centers, i.e. the F, O and C atoms, induces weak basicity and a weak nucleophilic character. The stability of the covalent bonds furthermore leads to an extended region of redox stability, in particular at anodic potentials. The alkali metal salts, and especially the lithium salts, derived from perfluorosulfonylmethanes are in particular usable for forming solid solutions with macromolecular materials of the polyether type, the said solid solutions being employed as solid polymer electrolytes in the production of primary or secondary all solid state thin-film generators.

These compounds $Mg[(R_FSO_2)_2CH]_y$ are obtained directly from $R_FSO_2F$ by reaction with the organomagnesium compound $CH_3MgCl$ in THF [R. J. Koshar & R. A. Mitsch J. Org. Chem. 38.3358 (1973), DE 2,012,011 and U.S. Pat. No. 3,776,960].

However, the organomagnesium compounds are difficult to handle because they are air-sensitive. Moreover, they are expensive.

A new process for the synthesis of symmetrical sulfonylmethanes from sulfonyl halides and ionic carbides, which are widely used and easy-to-handle products, has now been found. This process is extremely simple at any scale and uses carbides, which are low-cost and easy-to-handle compounds (solids) and are easily obtained by direct reaction of the elements (carbon+metal).

The invention relates to a process for the synthesis of sulfonylmethanes or derivatives thereof of the formula:

$$M[(RSO_2)_2CH]_m \qquad (I)$$

in which M represents H, an alkali metal, an alkaline earth metal, a quaternary ammonium anion $NR'_4$, in which the radicals R', identical or different, are monovalent organic radicals chosen from aliphatic radicals having 1 to 8 carbon atoms, aryl or alicyclic radicals having 3 to 8 carbon atoms, R represents a monovalent organic radical chosen from aliphatic radicals having 1 to 8 carbon atoms, aryl or alicyclic radicals having 3 to 8 carbon atoms and m represents the valence of M, which process is characterized in that an ionic carbide chosen from aluminum carbide, beryllium carbide, thorium carbide or uranium carbide is reacted with a sulfonyl halide of the general formula $RSO_2X$, in which R has the meaning given above and X is Cl or F, the reaction between the ionic carbide and the sulfonyl halide being carried out in a polar aprotic solvent, the product obtained is hydrolyzed, a compound of the formula $M_yY_m$ is added to the reaction medium before or after hydrolysis, in which M and m have the above meaning, Y represents an anion capable of reacting with the cation of the ionic carbide to form a compound which can be separated from compound (I), and y represents the valence of Y.

The process is carried out at a temperature between 0° C. and 150° C. In general, a temperature below 40° C. is appropriate.

The ionic carbides suitable for the process of the invention are compounds which contain the moiety $C^{4-}$ and are easily hydrolyzed with the formation of $CH_4$.

Of these carbides, aluminum carbide is particularly preferred because it is easily accessible and nontoxic.

The reaction of aluminum carbide with a sulfonylhalide gives an aluminum sulfonyl carbide which is difficult to isolate, due to the strong interaction of the aluminum ions with the solvents. However, this compound is advantageously used as obtained in solution as an intermediate for the synthesis of compounds (I).

When the compound (I) to be synthesized is a sulfonylmethane derivative $M[(RSO_2)_2CH]_m$, a salt of the formula $M_yY_m$, where M is different from H, is added to the reaction medium. The anion Y is chosen in such a manner that the aluminum salt formed with this anion can be separated from the final sulfonylmethane derivative. Carbonates, fluorides and phosphates are particularly preferred, since their aluminum salt is insoluble in water and in most of the solvents for sulfonylmethanes. Accordingly, it can be separated by filtration.

When compound (I) to be synthesized is a sulfonylmethane $(RSO_2)_2CH_2$, compound $M_yY_m$ is an acid $H_yY$. Preferably, $H_yY$ is a nonvolatile acid, such as sulfuric acid or phosphoric acid.

The process can also be carried out by using a chloride as $M_yY_m$. However, in such a case, it is more difficult to remove the aluminum chloride obtained because its solubility is very close to that of the desired compounds. In this case, the aluminum chloride must be converted to HCl and another aluminum salt by adding a strong acid, such as $H_2SO_4$ or $H_3PO_4$. This leads to the formation of an aluminum salt which precipitates, and HCl can be separated from the sulfonylmethane or its derivative by fractional distillation, since their respective boiling points are very different.

In the sulfonyl halide $RSO_2X$ used, the radical R can be a chlorinated or fluorinated radical. The fluorinated radicals are of particular interest in electrochemistry, especially for generators. The radicals R which are of particular interest are perfluorinated alkyl radicals having 1 to 4 carbon atoms.

The polar aprotic solvents can be chosen from ethers, such as tetrahydrofuran (THF), dimethoxyethane (DME), and glymes; amides, such as dimethylformamide (DMF), N-methylpyrrolidone (NMP), tetramethylurea (TMU), dimethylethyleneurea (DMU), tetraethylsulfonamide (TESA), and dimethyl sulfoxide (DMSO).

When the sulfonyl halide used for the reaction is a sulfonyl fluoride, it is preferred to use the ethers DME and THF, which constitute media which are sufficiently solvating for a rapid reaction to take place. When the sulfonyl halide used is a chloride, it is necessary to use very polar solvents of the amide type, in pure form or in the form of mixtures with ethers.

The hydrolyzing agent is preferably chosen from water, hydrochloric acid, sulfuric acid or phosphoric acid.

When the product to be synthesized is a sulfonylmethane $(RSO_2)CH_2$, the hydrolyzing agent is advantageously chosen from sulfuric acid and phosphoric acid. It can also fulfill the function of the compound $M_yY_m$.

The process according to the invention makes many sulfonylmethane salts easily accessible from ionic carbides, and especially from aluminum carbide.

The present invention is described in more detail by way of the examples which follow and which are given for non-limiting illustration.

EXAMPLE 1

Preparation of the potassium salt of bis(trifluoromethanesulfonyl)methane 22 ml of trifluoromethanesulfonyl chloride were added to a suspension of 4.8 g of aluminum carbide and 24 g of potassium fluoride in 200 ml of a mixture of DMF and DME (50/50). The reaction took place with stirring at standard temperature over a period of 72 hours. After adding 20 ml of water, the suspension was filtered, and then evaporated in vacuo. After extraction with acetone, 23 g of the potassium salt $K(CF_3SO_2)_2CH$ were obtained, which corresponds to a yield of 72%.

EXAMPLE 2

Preparation of the sodium salt of bis(trifluoromethanesulfonyl)methane 304 g of trifluoromethanesulfonyl fluoride were introduced into an autoclave containing 48 g of aluminum carbide as a fine powder suspended in 450 ml of diglyme and maintained at $-20°$ C. The reactor was sealed and stirred at a temperature of 100° C. until a pressure drop in the reactor was observed. After cooling and opening of the reactor, 300 ml of water containing 120 g of sodium carbonate were added. The solution was filtered and evaporated to give 250 g of the sodium salt $Na(CF_3SO_2)_2CH$.

EXAMPLE 3

Preparation of bis(trifluoromethanesulfonyl)methane 20 g of the sodium salt from Example 2 treated with 5 cc of anhydrous sulfuric acid. Distillation under reduced pressure (130° C./$1.3 \times 10^4$ Pa) gave 17 g of TSFM $(CF_3SO_2)_2CH_2$, which corresponds to a yield of 91%.

EXAMPLE 4

Direct preparation of bis(perfluorobutanesulfonyl)methane 302 g of perfluorobutanesulfonyl fluoride were added to an autoclave containing 24 g of aluminum carbide suspended in a mixture of equal volumes of diglyme and TMU. The reactor was sealed and maintained at 80° C. for 72 hours. After cooling, 200 ml of water acidified with 50 ml of sulfuric acid were added. 250 g of a solid which is the compound $(C_4F_9SO_2)_2CH_2$ were then extracted with ether.

The salts of other metals can be obtained by treatment with the corresponding metals, oxides, hydroxides and carbonates.

The process according to the invention thus makes it possible to synthesize directly a large number of sulfonylmethanes or derivatives thereof from easily accessible and low-cost reactants by using an anionic carbide.

A sulfonylmethane can be prepared from a derivative obtained directly by reaction with an acid (See Example 3).

A cation derivative of a sulfonylmethane can e obtained by direct (Example 4) or indirect (Example 2) treatment of sulfonylmethane with the corresponding metals, oxides, hydroxides or carbonates of the desired cation.

I claim:

1. A process for the synthesis of sulfonylmethane or derivatives thereof of the formula I:

$M[(RSO_2)_2CH]_m$ wherein M is at least one member selected from the group consisting of hydrogen, alkali metal, alkaline earth metal, quaternary ammonium anion $NR'_4$, wherein moiety $R'$ are at least one member selected from the group consisting of $C_1$–$C_8$ aliphatic, $C_3$–$C_8$ aryl and $C_3$–$C_8$ alicyclic, wherein R is at least one member selected from the group consisting of $C_1$–$C_8$ aliphatic, $C_3$–$C_8$ aryl and $C_3$–$C_8$ alicyclic, and wherein m represents the valence of M; said process comprising the steps of:

(a) reacting an ionic carbide with a sulfonyl halide of the general formula $RSO_2X$ in a polar aprotic solvent, wherein said ionic carbide is at least one member selected from the group consisting of aluminum carbide, beryllium carbide, thorium carbide and uranium carbide, and wherein X is at least one member of the group consisting of Cl and F, and wherein R is as defined above;

(b) hydrolyzing the product obtained from said reaction;

(c) adding a compound of the formula $M_yY_m$ to the reaction mixture before or after said hydrolysis step, wherein M and m are as defined above, and Y is an anion capable of forming an insoluable compound with a cation of said ionic carbide and wherein y represents the valence of Y, $M_yY_m$ being an acid $H_yY_m$ when M is H and the compound to be synthesized is a sulfonylmethane of the formula $(RSO_2)CH_2$.

2. The process of claim 1, wherein hydrolysis of process step (b) is accomplished by reaction with at least one member selected from the group consisting of water, hydrochloric acid, sulfuric acid and phosphoric acid.

3. The process of claim 1, wherein said ionic carbide is aluminum carbide.

4. The process of claim 1, wherein R is chlorinated.

5. The process of claim 1, wherein R is fluorinated.

6. The process of claim 1, wherein R is a perfluorinated $C_1$–$C_4$ alkyl.

7. The process of claim 1, wherein said compound $M_yY_m$ is a salt of an alkali metal.

8. The process according to claim 1, wherein the compound $M_yY_m$ is a salt of an alkaline earth metal.

9. The process of claim 1, wherein $M_yY_m$ is a salt of a quaternary ammonium anion $NR'_4$ wherein $R'$ are at least one member selected from the group consisting of $C_1$–$C_8$ aliphatic, $C_3$–$C_8$ aryl and $C_3$–$C_8$ alicyclic.

10. The process of claim 1, wherein the compound $M_yY_m$ is a non-volatile acid $H_yY$.

11. The process of claim 1, wherein said polar aprotic solvent is at least one member selected from the group consisting of ethers, amides and dimethylsulfoxide.

12. The process of claim 11, wherein said polar aprotic solvent is at least one member selected from the group consisting of tetrahydrofuran, dimethoxyethane, glymes, dimethylformamide, dimethylpyrrolidone, tetramethylurea, dimethyleneurea, tetraethylsulfonamide and dimethylsulfoxide.

13. The process of claim 10, wherein the sulphonylmethane is further reacted with a member selected from the group consisting of a metal, metal oxide, metal hydroxide and metal carbonate, thereby yielding the corresponding metal/sulphonylmethane salt.

14. The process of claim 10, wherein said nonvolatile acid is at least one member selected from the group consisting of sulfuric acid and phosphoric acid.

* * * * *